US006350719B1

(12) United States Patent
Kroll et al.

(10) Patent No.: US 6,350,719 B1
(45) Date of Patent: Feb. 26, 2002

(54) COMPOSITION FOR PREVENTING FROST DAMAGE TO PLANTS

(76) Inventors: Joseph Kroll, 4475-A Willow Pond Rd., West Palm Beach, FL (US) 33417; Richard W. Weinert, 850 Bella Vista Ct. South, Jupiter, FL (US) 33477

( * ) Notice: Subject to any disclaimer, the term of this patent is extended or adjusted under 35 U.S.C. 154(b) by 0 days.

(21) Appl. No.: 09/550,269

(22) Filed: Apr. 17, 2000

(51) Int. Cl.⁷ .................. A01N 25/32; A01N 59/00; A01N 59/08; A61K 33/14
(52) U.S. Cl. .................. 504/103; 504/123; 424/665
(58) Field of Search .................. 504/103, 123; 424/665

(56) References Cited

U.S. PATENT DOCUMENTS

| | | | | | |
|---|---|---|---|---|---|
| 4,986,925 A | * | 1/1991 | Fiske | .................. | 252/70 |
| 5,635,101 A | * | 6/1997 | Janke et al. | .................. | 252/70 |

\* cited by examiner

Primary Examiner—Alton Pryor
(74) Attorney, Agent, or Firm—Malloy & Malloy, P.A.

(57) ABSTRACT

A composition and method of protecting plants such as citrus trees, as well as other fruits and vegetable plants from damage due to exposure to frost during periods characterized by a rapid drop in ambient air temperature. The composition is formulated and applied in a manner which facilitates the formation of a coating on the exterior surfaces of the plant, thereby preventing direct contact of the frost with the exterior of the plant and preventing cellular degeneration. The composition is further formulated to have a sufficient viscosity to accomplish adequate coating yet assure easy removal during periods of rainfall or irrigation by sprinkling. The composition comprises a lignin sulfonate, which serves to regulate viscosity and a chloride salt brine solution, such as magnesium chloride, to reduce the freezing temperature. A significant bulk of the composition comprises any one of a plurality of organic by-products having sufficient nitrate content to be of nutritional benefit to the surrounding soil in which the plant is grown, wherein such organic by-products includes steepwater solubles, vintners' condensed solubles, brewers' condensed solubles, distillers' condensed solubles and whey.

22 Claims, No Drawings

COMPOSITION FOR PREVENTING FROST DAMAGE TO PLANTS

BACKGROUND OF THE INVENTION

1. Field of the Invention

This invention relates to a protective composition and its method of application to a variety of plants particularly, but not exclusively, fruit and vegetable plants, wherein the plants are protected from damage due to exposure to frost during conditions of reduced temperatures conditions. The composition is applied by forming a coating over the exterior surfaces of the plant, such as by spraying or other applicable means, thereby assuring that the frost will form on the protective coating rather than come into direct contact with the exterior surface portions of the plant which have been coated. Cellular degeneration of the coated parts of the plant is thereby prevented or significantly reduced. Removal of the coating is easily accomplished by natural rainfall or by sprinkling the plant utilizing conventional irrigation methods.

2. Description of the Related Art

In the agricultural industry it is well recognized that the growing or cultivation of certain crops is generally limited to those areas of the country which enjoy a moderate climate. For example, the production of citrus in the United States is primarily conducted in Florida and certain parts of Southern California, where temperatures infrequently reach the freezing point of 32° Fahrenheit. In addition, on the occasions when the temperature drops to the freezing point, the fruit and vegetable crops are not usually damaged, by being frozen, since temperatures in these areas of the country do not normally stay in the critical range of approximately 28 to 32 degrees Fahrenheit for extended periods. However, citrus plants as well as other fruits and vegetable plants are occasionally subjected to destructive damage due to frost which typically is caused by a rapid drop in ambient air temperature. Damage from frost is the result of ice crystals directly contacting and being able to physically invade the plant cells. The ice crystals can damage the invaded cell membrane to a sufficient degree that the cell is physically destroyed. Accordingly, it is well recognized that exposure to frost causes the loss of a significant percentage of citrus crops, as well as other tree fruit and vegetable crops, almost every year.

Susceptibility to frost damage depends not only on the ambient temperature but, at least to a certain extent, on a tree's stage of development, plant variety, physical location, etc. In order to prevent or at least lessen the loss of crops due to frost damage, a number of preventative measures have been developed. However, only a few frost protection methods have been consistently effective over the years. Accordingly, while conventional or known methods of frost protection are currently being practiced, such known methods vary considerably in cost, management time and effectiveness. The inefficiency and/or excessive cost of known technics is evidenced by the fact that their implementation may be more expensive and/or time consuming then the actual economic loss caused by frost damage to the various corps in question. Therefore, the average annual loss of crops to a grower or farmer due to frost damage, while significant, may not justify the time and money required in implementing one or more of the conventional frost protection systems currently available.

The various protection systems or methods undertaken largely depend on the variety of crops, location, etc. This is due to the fact that temperatures at which fruit buds are typically damaged, depends primarily on their stage of development. Naturally, as flowers began to swell and expand into blossoms, they become less resistant to damage from frost contact. However, it is also known that not all blossoms on a tree are equally susceptible. Resistance to frost damage varies within trees as it does between orchids, cultivators and crops. Buds that develop slowly tend to be more resistant. Therefore, it has been known for sometime that some trees or crops suffer weather damage at higher temperatures, while others are resistant at much lower temperatures. While prolonged cool weather tends to increase the hardiness of the plant, depending upon the type of fruit or vegetable plant involved, damage caused by the actual freezing of the plant is limited to the relatively unusual situations where temperatures remain below freezing, such as from 10° Fahrenheit to 28° Fahrenheit, for prolonged periods of at least 3 to 4 days.

One well recognized and often utilized method of protection is the application of water to both fruit and vegetable plants. Water, when appropriately applied, serves to "blanket" the plant thereby protecting the cell walls of the plant. Farmers and agriculturists, while using this method particularly on citrus crops, as well as other fruit and vegetable crops, understand that some damage may still occur. However, such damage is normally considered to be "acceptable" in comparison to the resulting damage when no protection system is used at all. While not completely effective, the use of water to protect plants from cold has increased over the last twenty years, apparently due to the cost, management and labor required in the use of heaters or other known methods, especially when attempting to protect an extended agricultural area, such as a citrus grove. Therefore, while the use of water lowers expenses and reduces environmental damage, when compared to heating or other methods, the proper application of water is important to its effectiveness. For example, the over use of water often times involves a risk of additional damage to the crop being protected. Extended water use may saturate soils and thereby increase the likelihood of diseases. Water over use may also cause the build up of ice on citrus trees or other plants to the extent where the trees are physically damaged.

Therefore, while water may be a preferred means of protection, it must be applied with proper care. Accordantly, "overtree sprinkling" has gained popularity, particularly in the citrus industry, wherein water is applied by a sprinkler network or system over the tops of the trees. Water is then allowed to freeze on the trees causing the heat released from the freezing water to maintain the temperature of certain portions of the tree near freezing, but not at or below the temperature where significant damage from freezing occurs. Also, successful overtree sprinkling depends to a great extent on the rate at which water is applied being balanced against the rate at which the water freezes, so that the temperature of the protected portions of the tree will remain at least a few degrees above the critical temperature at which damage occurs. Also, other significant problems exist with the use of overtree sprinkling in that the amount of water utilized depends on temperature, wind speed and a variety of other factors.

Another method of protection is known as "undertree" sprinkling and is gaining acceptance in the protection of fruit trees from frost. While considered to be at least partially effective, the reasons why undertree sprinkling works is not completely understood. It is believed that heat released as water vapor is condensed on leafs and blossom keeps temperature above the critical level, at which frost will not form. This approach uses less water and there is little or no chance of damage to the tree, as a result of ice built-up. However, certain blossoms or portions of the tree, especially those at the top of the tree, may not receive adequate protection.

Other methods commonly utilized in the protection of fruit and vegetable plants from frost involve the use of wind machines. The effectiveness of this method is based on the fact that the lowest several hundred feet of the atmosphere become stratified during calm, clear, frost prevalent conditions. An inversion condition thereby exists, meaning that temperature increases as it rises to the top of an inversion layer. The use of a plurality or network of wind machines serves to mix the warmer air from the upper portion of the inversion layer with the colder air near the ground. This has the effect of raising the overall air temperature around trees, at least by a few degrees and hopefully above the critical, damaging temperature levels. However, wind machines are motor driven and therefore consume fuel, although nearly not as much as "stack heaters". Also wind machines are only effective during calm, clear conditions and when frost conditions are not severe. Wind machines have been found to be ineffective under cold, windy conditions because the wind usually mixes the atmosphere enough to prevent an inversion layer from developing.

Based on the above, it is obvious that there is a need in the agricultural industry for a system which efficiently, adequately and inexpensively provides frost protection to a variety of different fruit and vegetable plants in a manner which will significantly reduce, if not completely eliminate, loss of crops during reduced temperature conditions. In addition, such an improved protection system should be relatively easy to apply, when compared to current protection systems, and effective in protecting a variety of plants from frost damage.

SUMMARY OF THE INVENTION

The present invention is directed to a composition for the prevention of frost damage to plants, such as citrus trees but which is sufficiently versatile to be applied to a variety of fruit and vegetable plants, without causing damage to the plant or the surrounding soil in which they are grown. The protective composition of the present invention and the method of its application significantly reduce the destruction of cells resulting from frost coming into direct contact with various exposed surfaces of the plant, including the leafs, branches, fruit, buds, etc.

It is well accepted that frost which is typically caused by a rapid drop in ambient air temperature, is a relatively common occurrence, even in various geographical areas throughout the world which enjoy mild to moderate climates. The protective composition of the present invention provides a unique method of protection by effectively "coating" exterior surfaces of various portions of the plant, in a manner which prevents or significantly reduces the possibility of frost coming into direct contact with the coated exterior surfaces. Cellular destruction of the plant is thereby significantly reduced. In addition, the protective composition, as well as its method of application, are designed to allow easy removal of the protective coating from the exterior surfaces of the plant to which it is temporarily adhered. Therefore, interference with photosynthesis or the other natural processes of the plant, is prevented.

More specifically, in order to effectively protect the exterior surfaces of the plant, the composition of the present invention incorporates a viscosity regulating ingredient specifically included in the formulation to facilitate the "coating" aspect of applying the composition. Accordingly, the viscosity of the composition is such that the coating applied to the exterior surface of the plant provides a protective "blanket" which, as set forth above, eliminates or significantly reduces the possibility of frost engaging the exterior surfaces of the plant which are coated. Instead, the formation of frost occurs in overlying relation to the protective coating of the composition. The viscosity regulating ingredient is also formulated into the protective composition, so as to facilitate the removal of the applied coating simply by exposure to natural rainfall. Alternatively, the protective coating can be easily removed by "overtree" sprinkling or other conventional methods of irrigation used in citrus groves, as well as other agricultural facilities involved with the production of a large variety of fruit and vegetables, other then citrus. The natural or intentional removal of the coating of the protective composition in a timely fashion eliminates the possibility of interfering with the normal biological processes of the plant such as photosynthesis.

The viscosity regulating agent preferably comprises a lignen sulfonate in predetermined quantities, to be described in greater detail hereinafter, properly formulated with the other ingredients of the protective composition to provide the proper viscosity to the composition without rendering it overly "tackey". Excessive viscosity of the composition would render it significantly more difficult to remove, especially when primarily relying on the natural occurrence of rainfall.

The protective composition of the present invention further includes an ingredient which serves to reduce the temperature at which freezing will occur. Preferably, the freezing temperature reducing ingredient comprises a chloride salt brine such as, but not necessarily limited to, magnesium chloride. The chloride salt brine is formulated into the composition in sufficient quantities to reduce the temperature at which freezing occurs. However, the quantity utilized should be limited and maintained within predetermined parameters, which would not damage the plant due to over exposure to a salt based ingredient.

The protective composition of the present invention further includes a sufficient quantity of at least one bulk ingredient, which is preselected from a group of organic by-products. Each of the preselected organic by-products are characterized by being environmentally friendly, biodegradable, cost competitive and readily available in large quantities. In addition, when properly formulated into the protective composition of the present invention, any one of these by-products may serve as a nutritional additive to the plant and/or surrounding soil in which the plant is grown, when the coating of the composition is removed from the plant.

The preselected group of organic by-products comprises steepwater solubles, vintners, condensed solubles, brewers, condensed solubles, distillers I condensed solubles, and whey. When formulated, the protective composition of the present invention therefore comprises at least one by-product selected from this group.

In one embodiment, the protective composition of the present invention may include the viscosity regulating agent and the freeze temperature reducing agent blended in a mixture of steepwater solubles. Steepwater solubles are by-products of a milling process of grains, such as in the wet milling of corn or other grains including rice, barely, oats, etc.

In another embodiment of the present invention the above set forth ingredients are combined with the organic by-product comprising vintners' condensed solubles which are by-products from the formation and production of wine from grapes and other fruits as well as from grains including, for example rice.

In yet another embodiment of the present invention, one of the preselected organic by-products includes brewers' condensed solubles which are a by-product of the brewing process of the grains used to create brewed beverages, such as beer.

In yet another embodiment of the present invention, a preselected organic by-product capable of being used in the formulation of the protective composition of the present invention includes distillers' condensed solubles which are by-products from the distillation and production of alcohol from starches and sugars, including molasses, cane sugar, beet sugar as well as wet and dry grains including corn, milo, barley, rye and, rice.

Also, in yet another embodiment of the protective composition of the present invention in the included preselected organic by-product is whey. Whey is a by-product from the process of cheese making.

Each of the above set forth organic by-products also have common characteristics which facilitate their individual or combined use in the formulation of the protective composition. Such preferred characteristics include being water soluble, inexpensive, widely available in large quantities, biodegradable, environmentally safe and nutritionally beneficial, when deposited into the soil in which the plants being protected are grown. The nutritional benefits of these by products are attributable to their containment of sufficient quantities of nitrates.

These and other objects, features and advantages of the present invention will become more clear when the detailed description is taken into consideration.

DETAILED DESCRIPTION OF THE PREFERRED EMBODIMENT

The present invention is directed towards a composition for the prevention or significant reduction of frost damage in a variety of different types of plants, particularly citrus trees. However, the protective composition of the present invention is applicable to a variety of other plants, including numerous fruit and vegetable producing plants. As will be explained in greater detail hereinafter, the present invention also includes a method of application of the protective composition in a manner which facilitates its coating over exterior surface portions of the plant being protected, thereby forming a protective "blanket" which prevents or significantly reduces the possibility of frost directly contacting exterior surface portions of the plant. Cellular destruction of the plant due to direct contact with frost having formed thereon is thereby prevented.

Accordingly, the protective composition of the present invention comprises a viscosity regulating agent preferably in the form of lignin sulfonate. The viscosity regulating agent is present in the composition in predetermined, quantities which assures that the viscosity of the resulting protective composition is sufficient to effectively coat intended exterior surfaces of the plant being protected. In addition, the viscosity is regulated to the extent that the coating can be easily removed either by natural rainfall or by overtree sprinkling or other conventional means of irrigation applied to the plant being protected. Easy removal of the composition from its overlying relation to exterior surface portions of,the plant is important, so as to not interfere with the normal functioning or processes of the plant, such as photosynthesis. The use of a lignin sulfonate as the viscosity regulating ingredient may include, ammonium lignin sulfonate, sodium lignin sulfonate and calcium lignin sulfonate. Depending upon a variety of other factors the lignin sulfonate is present in the final composition in quantities of substantially between 3% by weight to 25% by weight.

The protective composition of the present invention further comprises an ingredient to regulate or more specifically to lower the freezing temperature. Such additional ingredient includes a chloride salt urine such as magnesium chloride. In addition, other chloride salt brines of the type applicable for formulation into the protective composition of the present invention include calcium chloride and sodium chloride. The preferred chloride salt brine, magnesium chloride, is present with the other ingredients of the composition of the present invention in quantities of substantially between 2% and 15% by weight.

In addition to the above, the remainder of the composition of the present invention comprises at least one bulk ingredient, more specifically defined by one or more preselected organic by-products. The one or more organic by-product ingredients are present in quantities of substantially 95% to 60% by weight of the final protective composition. More specifically, the pre-selected organic by-products may include steepwater solubles, vintners' condensed solubles, brewers' condensed solubles, distillers' condensed solubles and whey. All of the above noted organic by-products include common characteristics which make them, either individually or in combination with one another, an important part of the formulation of the protective composition. Such common characteristics include being non-hazardous to humans or animals, environmentally friendly, biodegradable, inexpensive, and readily available in large quantities In addition, each of the organic by-products which collectively define the group as set forth above, contain a sufficient amount of nitrates to be nutritionally beneficial to the soil surrounding the plants to which the composition is applied. Such nutritional benefits may be considered to be of particular importance when the composition is removed from the plant, as will be discussed hereinafter, and deposited in the surrounding soil in which the plants are grown.

Accordingly, one embodiment of the present invention includes the use of steepwater solubles as the one organic by-product included with the viscosity regulating and temperature reducing ingredients, as set forth above. Steepwater solubles are a well known and commercially available by-product of a milling process of grains including, for example, the wet milling of corn, wheat, sorghum, barley and soy beans. The wet milling process referred to is commercially known and practiced extensively in the production of staple products including, but not limited to, corn oil, corn syrup, dexterous, dry starches and animal feed. The wet milling process referred to comprises the procedural steps of steeping, milling, recovering and processing. During the steeping process, kernels of corn, by way of example, are softened by soaking them in a solution normally containing small amounts of sulfuric dioxide or like acidic components, except when wet milling wheat. The softened kernels are separated from the steepwater and further processed to obtain the various primary or end products, as set forth above. The remaining steepwater contains solubles which, subsequent to evaporation, are recovered for use as nutritional additives for such additional products as animal feeds. Steepwater solubles can be utilized, in the present invention, in the form obtained from the wet milling process, wherein the water content of the steepwater solubles may vary from 50% to as little as 1–2%, the latter being preferable to reduce transportation costs.

Another embodiment of the present invention comprises the inclusion of vintners' condensed solubles as the organic by-product which is formulated in the composition of the present it invention. Vintners' condensed solubles are a by-product of the fermentation and production of wine from grapes and other fruits and also from grains, such as rice, used in the production of "sake" and other rice wines. The fermentation process includes fermenting liquids that are extracted from the fruit or grain in resulting from the fermentation process, solubles settle to the bottom of the wine vat or container. These bottom liquids may be concentrated at substantially 50% solubles which, after the liquid is evaporated or dried, are recovered typically for use as additives in fertilizers, mulching material, and as nutritional additives in animal feeds. The vintners' condensed solubles can be utilized in the form obtained directly from the fermentation process or dried so as to have a water content of as much as 50% by weight or as little as 1% to 2% by weight.

Another embodiment of the protective composition of the present invention includes the use of brewers' condensed solubles as at least one of the organic by products. This organic by-product is created from the brewing process used to produce beer as well as other brewed beverages. Upon completion or during a typical brewing process, the brewed beverage can be removed, leaving behind a residue of yeast, unfermented wort as well as other solubles. This residue contains soluble ingredients which, after the residue is evaporated or dried, are recovered for use as nutritional additives in animal feeds and as additives for other products.

Another embodiment of the protective composition of the present invention includes the use of distillers' condensed solubles as the preselected organic by-product. In the conducting of a typical distillation process, such as in the production of alcohol, the fermentation of starches or sugars is accomplished utilizing a microorganism defined by a specialized strain of yeast. The yeast is a subsequently separated from a resulting mash and the alcohol produced thereby is removed by distillation. The mixture remaining after removal of the alcohol, as well as most of the yeast, is referred to as distillers' condensed solubles. This organic by-product is also known in the distilling industry as "swill" or "stillage". The resulting residue contains solubles which, after being subjected to an evaporating or drying process, are recovered for nutritional additives and utilized in animal feeds. As set forth above distillers' condensed solubles are the by-product resulting from the distillation and production of alcohol from starches and sugars which may include, by way of example, molasses, cane sugar and beet sugar, as well as the various wet and dried milled grains, including corn, barely, rice, etc.

Yet another embodiment of the protective composition of the present invention comprises the inclusion of the organic by-product, whey. Whey is a by-product of the cheese making process which comprises adding a coagulating agent to the various milks used in the production of cheese or alternatively allowing the milks to naturally coagulate and then removing all of the coagulated matter for further processing. The liquid remaining after the coagulation and straining process is commonly known in the cheese industry as whey. As with the other preselected organic by-products set forth above, an evaporating or drying process can be applied so as to vary the containment of solubles from as high as 50% to as low as 1–2%.

Accordingly, the present invention is directed to a composition which protects plants against frost damage and, including the various embodiments thereof, that comprises a viscosity regulating ingredient, preferably magnesium chloride; a temperature reducing ingredient, preferably a lignin sulfonate; and at least one organic by-product selected from the group consisting of steepwater solubles, vintners' condensed solubles, brewers' condensed solubles, distillers' condensed solubles and whey.

By way of example, a preferred embodiment of the present invention comprises a protective composition formulated to include substantially 10% by weight of a lignin sulfonate; 5% by weight of a chloride salt brine in the form of magnesium chloride and 85% by weight of at least one organic by-product selected from the group consisting of steepwater solubles, vintners' condensed solubles, brewers' condensed solubles and whey. In addition, experimentation in formulating the protective composition of the present invention indicated a difficulty in directly blending or mixing lignin sulfonate and the magnesium chloride with one another. Accordingly, the formation of the protective composition preferably comprises first mixing the lignin sulfonate with the steepwater solubles, when utilized as the selected organic by-product, and subsequently blending in the magnesium chloride, each ingredient being present in the quantities indicated above.

It was found that 10% by weight of the lignin sulfonate was preferred in the production of a protective composition having a sufficient viscosity to effectively coat intended exterior surface portions of the plant being protected, while at the same time allowing for effective removal of the protective coating, when the possibility of frost damage is no longer a danger. Easy and effective removal of the protective composition is important in order to eliminate the possibility of damage to the plant caused by leaving the protective coating on the plant for an extended period of time. Therefore, the coating may be removed in a timely fashion by means of natural rainfall or alternatively by overtree sprinkling or other conventional means of applying water to the exterior surface of the plant, including known irrigation techniques. Further, once the protective coating has been removed from the plant's surfaces, its absorption into the soil surrounding the plant may provide additional nutritional benefits, based on the containment of nitrates in the preselected group of organic by-products, which are incorporated into the formulation of the protective composition, as set forth above.

The method of applying the protective composition of the present invention is preferably accomplished by spraying a solution of the formulated composition in any applicable manner preferably in mist form in sufficient quantities over the trees to be protected, such that the exterior surface portions of the trees or plants, most vulnerable to frost damage, would be effectively coated. Accordingly, the method of application of the subject protective composition is meant to be incorporated within the spirit and scope of the present invention.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A method of protecting plants against frost damage comprising applying to the plant an aqueous solution of lignin sulfonate, magnesium chloride and at least one organic by-product ingredient selected from the group consisting of steepwater solubles, vintners' condensed solubles, brewers' condensed solubles, distillers' condensed solubles and whey.

2. A method as recited in claim 1 wherein said organic by-product comprises steepwater solubles.

3. A method as recited in claim 1 wherein said organic by-product comprises vintners' condensed solubles.

4. A method as recited in claim 1 wherein said organic by-product comprises brewers' condensed solubles.

5. A method as recited in claim 1 wherein said organic by-product comprises distiller' condensed solubles.

6. A method as recited in claim 1 wherein said organic by-product is whey.

7. A method as recited in claim 1 wherein said lignin sulfonate is present in quantities of between 3% and 25% by weight, said magnesium chloride is present in quantities between 2% and 15% by weight, and said organic by-product is present in quantities between 95% and 60% by weight.

8. A method as recited in claim 7 wherein said lignin sulfonate is present in quantities of substantially 10% by weight, said magnesium chloride is present in quantities of 5% by weight and said organic by-product is present in quantities of 85% by weight.

9. A method as recited in claim 8 wherein said aqueous solution is applied by spraying a mist onto exterior surface portions of the plant.

10. A method as recited in claim 1 further comprising applying the composition to the exterior of the plant wherein the composition has a range of viscosity sufficient to assure a coating of exterior surfaces of the plant and a removal of the coating therefrom during rainfall.

11. A composition for the prevention of frost damage to plants, said composition comprising:
   a) a viscosity regulating ingredient comprising a lignin sulfonate present in quantities between 3% and 25% by weight,
   b) a freeze temperature reducing ingredient comprising magnesium chloride present in quantities between 2% to 15% by weight, and
   c) an organic by-product comprising vintners' condensed solubles present in quantities between 95% to 60% by weight.

12. A composition for the prevention of frost damage to plants, said composition comprising:
   a) a viscosity regulating ingredient comprising lignin sulfonate present in quantities between 3% and 25% by weight,
   b) a freeze temperature reducing ingredient comprising magnesium chloride present in quantities between 2% to 15% by weight, and
   c) an organic by-product comprising brewers' condensed solubles present in quantities between 95% to 60% by weight.

13. A composition for the prevention of frost damage to plants, said composition comprising:
   a) a viscosity regulating ingredient comprising lignin sulfonate present in quantities of substantially between 3% and 25% by weight,
   b) a freeze temperature reducing ingredient comprising magnesium chloride present in quantities between 2% to 15% by weight, and
   c) an organic by-product comprising whey present in quantities between 95% to 60% by weight.

14. A composition for the prevention of frost damage to plant, said composition comprising:
   a) a viscosity regulating ingredient comprising lignin sulfonate present in quantities between 3% and 25% by weight,
   b) a freeze temperature reducing ingredient comprising magnesium chloride present in quantities between 2% to 15% by weight, and
   c) an organic by-product comprising distillers' condensed solubles present in quantities between 95% to 60% by weight.

15. A composition for the prevention of frost damage to plants, said composition comprising:
   a) a viscosity regulating ingredient comprising a lignin sulfonate,
   b) a freeze temperature reducing ingredient comprising magnesium chloride, and
   c) an organic by-product comprising at least one ingredient selected from the group consisting of vintners' condensed solubles, brewers' condensed solubles, distillers' condensed solubles and whey.

16. A composition as recited in claim 15 wherein said lignin sulfonate is present in quantities between 3% and 25% by weight.

17. A composition as recited in claim 16 wherein said magnesium chloride is present in quantities between 2% to 15% by weight.

18. A composition as recited in claim 17 wherein said organic by-product is present in quantities between 95% and 60% by weight.

19. A composition as recited in claim 18 wherein said organic by-product comprises vintners' condensed solubles.

20. A composition as recited in claim 18 wherein said organic by-product comprises brewers' condensed solubles.

21. A composition as recited in claim 18 wherein said organic by-product comprises whey.

22. A composition as recited in claim 18 wherein said organic by-product comprises distillers' condensed solubles.

* * * * *